(12) United States Patent
Letinier et al.

(10) Patent No.: US 11,210,314 B2
(45) Date of Patent: Dec. 28, 2021

(54) DEVICE AND METHOD FOR GENERATING A DRUG DATABASE

(71) Applicants: UNIVERSITE DE BORDEAUX, Bordeaux (FR); CENTRE HOSPITALIER UNIVERSITAIRE DE BORDEAUX, Talence (FR); INSTITUT NATIONAL DE LA SANTE ET DE LA RECHERCHE MEDICALE—INSERM, Paris (FR)

(72) Inventors: Louis Letinier, Bordeaux (FR); Clément Goehrs, Bordeaux (FR); Sébastien Cossin, Merignac (FR); Bruno Thiao-Layel, Talence (FR); Frantz Thiessard, Gradignan (FR); Antoine Pariente, Talence (FR); Gayo Diallo, Lormont (FR); Vianney Jouhet, Merignac (FR)

(73) Assignees: UNIVERSITE DE BORDEAUX, Bordeaux (FR); CENTRE HOSPITALIER UNIVERSITAIRE DE BORDEAUX, Talence (FR); INSTITUT NATIONAL DE LA SANTE ET DE LA RECHERCHE MEDICALE—INSERM, Paris (FR)

( * ) Notice: Subject to any disclaimer, the term of this patent is extended or adjusted under 35 U.S.C. 154(b) by 250 days.

(21) Appl. No.: 16/461,776

(22) PCT Filed: Nov. 20, 2017

(86) PCT No.: PCT/EP2017/079810
§ 371 (c)(1),
(2) Date: Jun. 8, 2019

(87) PCT Pub. No.: WO2018/091714
PCT Pub. Date: May 24, 2018

(65) Prior Publication Data
US 2019/0361906 A1     Nov. 28, 2019

(30) Foreign Application Priority Data

Nov. 21, 2016 (FR) ..................... 1661257

(51) Int. Cl.
*G06F 16/25*     (2019.01)
*G16H 50/70*     (2018.01)
(Continued)

(52) U.S. Cl.
CPC .......... *G06F 16/254* (2019.01); *G06F 16/245* (2019.01); *G06F 16/9024* (2019.01); *G16H 50/70* (2018.01); *G16H 70/40* (2018.01)

(58) Field of Classification Search
CPC .. G06F 16/254; G06F 16/245; G06F 16/9024; G16H 50/70; G16H 70/40
See application file for complete search history.

(56) References Cited

U.S. PATENT DOCUMENTS

| 8,429,179 B1 | 4/2013 | Mirhaji |
| 2009/0037389 A1 | 2/2009 | Kothari et al. |

(Continued)

OTHER PUBLICATIONS

Castano et al., "Semantic dictionary design for database interoperability", Proceedings 13th International Conference on Data Engineering, vol. 1, pp. 43-54, 1997.
(Continued)

*Primary Examiner* — Truong V Vo
(74) *Attorney, Agent, or Firm* — BakerHostetler

(57) ABSTRACT

A device for generating a pivot drug database implemented in a computer system, the device includes an extraction unit configured for extracting the data from a set of elementary drug data sources, the elementary drug data sources storing drug-related data, each elementary data source being associated with a representation of the data; a structuring unit configured for structuring the extracted data by applying a pivot ontology to the extracted data, the pivot ontology
(Continued)

defining classes derived from one or more ontologies of the drug and relationships between the classes, which provides structured data associated with a graph representing the relationships between the classes corresponding to the structured data; the device being configured for generating the pivot drug database according to the graph and the structured data, the pivot database storing the structured data. Applications: drug interaction analysis tools, tool for assisting medical prescription.

12 Claims, 11 Drawing Sheets

(51) Int. Cl.
    *G16H 70/40*     (2018.01)
    *G06F 16/245*     (2019.01)
    *G06F 16/901*     (2019.01)

(56) References Cited

U.S. PATENT DOCUMENTS

2010/0318537 A1* 12/2010 Surendran ............... G06F 16/36
    707/759
2016/0179945 A1* 6/2016 Lastra Diaz ........ G06F 16/3334
    707/739

OTHER PUBLICATIONS

Lawrence, et al., "Integrating Relational Database Schemas using a Standardized Dictionary", 2001.

Chawathe, et al., "The TSIMMIS Project: Integration of Heterogenous Information Sources", Oct. 1994.

Reynaud, et al., "An application of the mediator approach to services over the Web", 2003.

Alani, et al., "Automatic ontology-based knowledge extraction from web documents", IEEE Intelligent Systems, vol. 18, Issue: 1, Jan.-Feb. 2003.

Cruz, et al., "The Role of Ontologies in Data Integration", 2005.

Ayvaz, et al., "Toward a complete dataset of drug-drug interaction information from publicly available sources", J. Biomed Inform., 55, Jun. 2015.

Noy, et al., "Ontology Development 101: A Guide to Creating Your First Ontology", Stanford Knowledge Systems Laboratory Technical Report KSL-01-05 and Stanford Medical Informatics Technical Report SMI-2001-0880, Mar. 2001.

Jiang, et al., "ADEpedia: a scalable and standardized knowledge base of Adverse Drug Events using semantic web technology", AMIA . . . Annual Symposium proceedings / AMIA Symposium, pp. 607-616, Jan. 1, 2011.

Chun, et al., "Social health data integration using semantic Web", SAC '12 Proceedings of the 27th Annual ACM Symposium on Applied Computing, pp. 392-397, Mar. 29, 2012.

Jonquet, et al., "The Open Biomedical Annotator", AMIA Summit on Translational Bioinformatics, Mar. 1, 2009.

Food and Drug Administration, "Structured Product Labeling > Section Headings (LOINC)", Feb. 9, 2016.

\* cited by examiner

| atc | labelatc | ATC2 | labelATC2 | labelatcx | dci | ANSM family |
|---|---|---|---|---|---|---|
| http://galen-project.com#0.3#C07AB04 | ACEBUTOL xsd string | http://galen-project.com#0.3#C07 | BETA BLOCKERS xsd string | acebutol | http://galen-project.com#0.3#acebutolcheба | anti-hypertensives except alpha blockers xsd string |
| http://galen-project.com#0.3#C07AB04 | ACEBUTOL xsd string | http://galen-project.com#0.3#C07 | BETA BLOCKERS xsd string | acebutol | http://galen-project.com#0.3#acebutolcheба | beta blockers (except esmolol and sotalol) xsd string |
| http://galen-project.com#0.3#C07AB04 | ACEBUTOL xsd string | http://galen-project.com#0.3#C07 | BETA BLOCKERS xsd string | acebutol | http://galen-project.com#0.3#acebutolcheба | beta blockers (except esmolol) xsd string |
| http://galen-project.com#0.3#C07AB04 | ACEBUTOL xsd string | http://galen-project.com#0.3#C07 | BETA BLOCKERS xsd string | acebutol | http://galen-project.com#0.3#acebutolcheба | bradycardics xsd string |
| http://galen-project.com#0.3#C07AB04 | ACEBUTOL xsd string | http://galen-project.com#0.3#C07 | BETA BLOCKERS xsd string | acebutol | http://galen-project.com#0.3#acebutolcheба | blood pressure lowering drugs xsd string |
| http://galen-project.com#0.3#M01AB16 | ACECLOFENAC xsd string | http://galen-project.com#0.3#M01 | ANTI-INFLAMMATORIES AND ANTI-RHEUMATOIDS xsd string | aceclonefac | http://galen-project.com#0.3#aceclonefaa1169 | non-steroidal anti-inflammatories xsd string |
| http://galen-project.com#0.3#M01AB16 | ACECLOFENAC xsd string | http://galen-project.com#0.3#M01 | ANTI-INFLAMMATORIES AND ANTI-RHEUMATOIDS xsd string | aceclonefac | http://galen-project.com#0.3#aceclonefaa1169 | hyperkalemics xsd string |
| http://galen-project.com#0.3#B01AA07 | ACENOCOUMAROL xsd string | http://galen-project.com#0.3#B01 | ANTI-THROMBOTICS xsd string | acenocoumarol | http://galen-project.com#0.3#acenocouma35da0 | oral anticoagulants xsd string |
| http://galen-project.com#0.3#B01AA07 | ACENOCOUMAROL xsd string | http://galen-project.com#0.3#B01 | ANTI-THROMBOTICS xsd string | acenocoumarol | http://galen-project.com#0.3#acenocouma35da0 | vitamin k antagonists xsd string |
| http://galen-project.com#0.3#S01EC01 | ACETAZOLAMIDE xsd string | http://galen-project.com#0.3#S01 | OPHTHALMIC DRUGS xsd string | acetazolamide | http://galen-project.com#0.3#acetazolame5052 | urinary alkalinizing agents xsd string |

FIGURE 5

Classes

BrandName

BrandName ⊑ Drug
BrandName ⊑ ¬ClinicalDrug
BrandName ⊑ ¬BrandedDrug

BrandedDrug

BrandedDrug ⊑ Drug
BrandedDrug ⊑ ¬BrandedName

BrandedDrugComponent

BrandedDrugComponent ≡ ∀ hasBrandedDose Dose ⊓ ≥ 1 hasBrandedDose Dose
BrandedDrugComponent ⊑ Drug

BrandedDrugForm
BrandedDrugForm ≡ ∀ hasBrandedDoseForm DoseForm ⊓ ≥ 1 hasBrandedDoseForm DoseForm
BrandedDrugForm ⊑ Drug

ClinicalDrug
ClinicalDrug ⊑ ClinicalDrugForm
ClinicalDrug ⊑ Drug
ClinicalDrug ⊑ ClinicalDrugComponent
ClinicalDrug ⊑ BrandName

ClinicalDrugComponent
ClinicalDrugComponent ≡ ∀hasDose Dose ⊓ ≥ 1 hasDose Dose
ClinicalDrugComponent ⊑ Drug

ClinicalDrugForm
ClinicalDrugForm ≡ ∀hasDoseForm DoseForm ⊓ ≥ 1 hasDoseForm DoseForm
ClinicalDrugForm ⊑ Drug

ComposedClinicalDrugComponent
ComposedClinicalDrugComponent ⊑ ClinicalDrugComponent

ComposedClinicalDrugForm
ComposedClinicalDrugForm ⊑ ClinicalDrugForm

ComposedPharmaceuticalIngredient
ComposedPharmaceuticalIngredient ⊑ PharmaceuticalIngredient

Dose

Dose Form

Drug

Drug ≡ ∃ hasIngredient PharmaceuticalIngredient
⊓ ∀ hasIngredient PharmaceuticalIngredient
⊓ ≥ 1 hasIngredient PharmaceuticalIngredient

PharmaceuticalIngredient
PharmaceuticalIngredient ≡ ∃ IngredientOf Drug

Unit

FIG. 12

DEVICE AND METHOD FOR GENERATING A DRUG DATABASE

CROSS-REFERENCE TO RELATED APPLICATIONS

This application is a National Stage of International patent application PCT/EP2017/079810, filed on Nov. 20, 2017, which claims priority to foreign French patent application No. FR 1661257, filed on Nov. 21, 2016, the disclosures of which are incorporated by reference in their entirety.

TECHNICAL FIELD

The present invention relates generally to data processing, and in particular to a device and a method for generating a drug database from a drug ontology model. It also relates to a device and a method of analysis based on such a database.

BACKGROUND

Major advances in "BIG Data" are in the process of revolutionizing healthcare. One of the health issues notably concerns the development of analytical tools relating to drugs such as tools for assisting medical prescription. Such tools are based on knowledge bases or databases appropriate for storing medical data and delivering data relating to a medical prescription, in a structured manner in response to queries. Such databases may also be used in pharmacovigilance tools for detecting, assessing and preventing adverse effects linked to the drugs. The information relating to the adverse effects of a set of drugs may be collected in an upstream observation phase conducted during the experimental stages, or during a downstream phase, e.g. in the marketing and use of drugs. This information may be recorded in different data sources in accordance with standardized terminology rules. These sources may then be connected to the knowledge bases used in the decision support tools for medical prescription.

Today there are numerous drug-related data sources, throughout the world. This data is produced by different bodies (National Agency for Drug Safety and Health Products—ANSM, the National Health Authority—HAS, Health Insurance etc.), according to various approaches. In such data sources, the data is organized and grouped according to specific classification and terminology rules. These data sources also exhibit heterogeneity at different levels.

Other less formalized data sources are also known. They are derived, for example, from social networks and discussion forums on health, and may be exploited for different uses.

International classifications are also known. Such classifications are common to all countries but exist in different versions, such as the Anatomical Therapeutic Chemical classification—ATC, published by the World Health Organization but used and adapted in some countries (Rønning et al., 2000).

Thus the existing data sources concerning drugs meet very heterogeneous classification, formalism and terminology rules, which complicates the exploitation of these multiple sources by a single knowledge base, e.g. for a medical prescription assistance application.

But the exploitation of these different drug-related data sources is fundamental to the development of effective tools for assisting medical prescription or pharmacovigilance support (detection of any unexpected relationship between a drug and a technical effect), for example. It may also be useful for application to tools for detecting new interactions between drugs (Ayvaz S. et al., 2015).

In known approaches to managing drug-related knowledge (Castano et al., 1997, Lawrence et al., 2001, Chawathe et al., 1994, Reynaud et al., 2003, Levy et al., 2001), ontology is used for formally representing the meaning of terms describing the adverse effects of drugs. The formal character of the representation in an ontology is suitable for the automated exploitation of knowledge by machines (Alani et al., 2003). It allows the integration and processing of heterogeneous data sources and the possibility of reasoning out and deducing new relationships or possible alignments between the existing data sources (Cruz et al., 2005).

There are no effective solutions today for integrating and dynamically analyzing semantically heterogeneous sources of knowledge in the drug domain appropriate for being used to generate recommendations in terms of medical prescription, where necessary taking drug interactions into account.

There is therefore a need for a device and a method for managing data originating from multiple data sources in heterogeneous format, notably for use in tools for assisting medical prescription or the analysis of drug effects.

SUMMARY OF THE INVENTION

The invention improves the situation by providing a device for generating a pivot drug database implemented in a computer system, the device comprising:
  an extraction unit configured for extracting the data from a set of elementary drug data sources, the elementary drug data sources storing drug-related data, each elementary data source being associated with a representation of the data;
  a structuring unit configured for structuring the extracted data by applying a pivot ontology to the extracted data, the pivot ontology defining classes derived from one or more ontologies of the drug and relationships between the classes, which provides structured data associated with a graph representing the relationships between the classes corresponding to said structured data;
  the device being configured for generating the pivot drug database according to the graph and the structured data, the pivot database storing the structured data.

In one embodiment, the extraction unit may be configured for retrieving the data of the elementary data sources in the form of a description file in an initial format, the extraction unit comprising a first parser configured for scanning the data of each description file in the initial format and a transformation function for transforming the description file in the initial format into a description file in a target format, from the scanned data.

The structuring unit may comprise a parser configured for scanning each description file in the target format and for searching for similarity information between the scanned data and the classes of the pivot ontology, the structuring unit being configured for applying the pivot ontology to the scanned data by associating it with classes and relationships according to the similarity information, the graph representing the classes and the links.

In one embodiment, the pivot ontology may comprise three main classes:
  A main class "Ingredient";
  A main class "Drug"; and
  A main class "Clinical Drug",
  the three main classes being independent.

The class "Drug" may advantageously be the top class and comprises a set of subclasses.

The subclasses may comprise a set of "clinical" type classes and a set of "commercial" type classes.

The top class "drug" may be connected by a relationship of the "possesses" type with the "Ingredient" class.

In particular, the pivot ontology may be represented according to a chosen query language.

A drug-related analysis device is further provided, comprising a server and the pivot database generated by the device according to one of the preceding features, the device being capable of querying the pivot database in response to at least one query received from a client device and returning the result to the client device.

The drug-related analysis device may be a device for assisting medical prescription.

As a variant, the drug-related analysis device may be a drug interaction analysis device.

A method for generating a pivot drug database is further provided, implemented in a computer system, the method comprising the steps of:
- selecting elementary drug data sources storing data relating to drugs, each elementary data source being associated with a representation of the data;
- extracting the data from said drug data sources;
- applying a pivot ontology to said extracted data, the pivot ontology defining classes derived from one or more ontologies of the drug and relationships between said classes, which provides structured data associated with a graph representing the relationships between the classes corresponding to the structured data;
- generating a pivot database from the graph and the structured data, the pivot database storing the structured data.

Other features and advantages of the invention will emerge with the aid of the following description and the figures of the appended drawings in which:

DESCRIPTION OF THE FIGURES

FIG. 5 depicts the results obtained by querying the pivot database according to one embodiment;

FIG. 12 lists a third example in pseudo-code mentioned in the description.

The drawings to the description basically comprise elements of a certain character. They may therefore not only serve to better elucidate the description, but also contribute to the definition of th invention, where appropriate.

DETAILED DESCRIPTION

The present invention provides a device and a method for generating a drug-related database for integrating multiple heterogeneous sources based on an ontological model.

Figure 1:
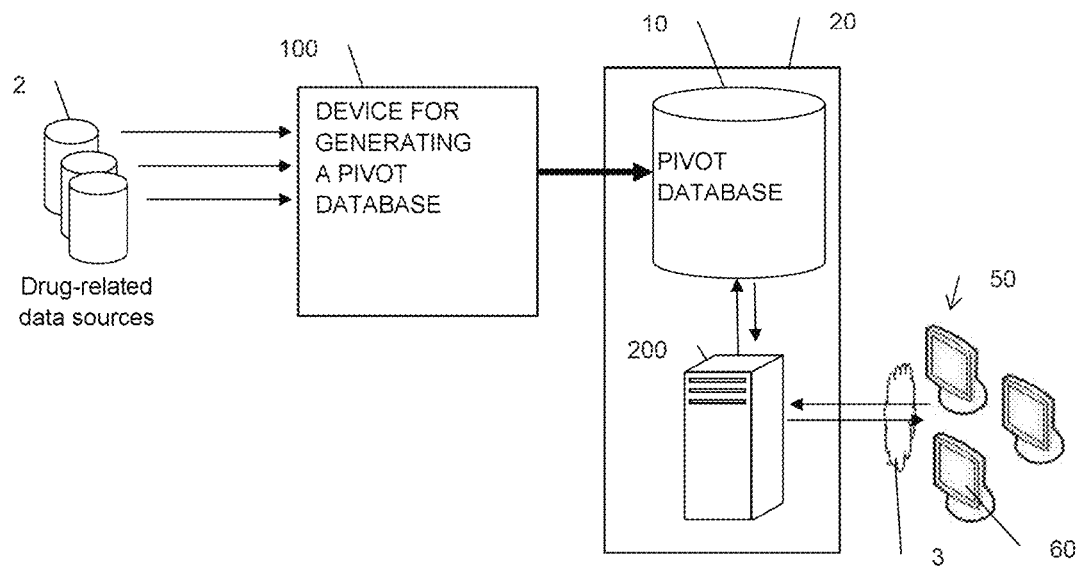
FIG. 1 is a diagram representing the device for generating the pivot drug database, according to some embodiments.

FIG. 1 represents an example of an environment in which the device 100 may be implemented for generating a pivot drug database 10 (also termed a "common" or "transverse" drug database) based on data extracted from a plurality of data sources 2, each data source storing the drug-related data in a format or an elementary structure specific to the source 2. The data sources 2 are selected beforehand.

As used here, a "database" also termed a "knowledge base" designates a computer tool making it possible to store and retrieve one or more pieces of data from the stored data by executing a query defined according to a query language.

To facilitate the understanding of some embodiments, additional definitions are provided below:

As used here an 'ontology' designates a semantic resource best defining a knowledge domain. An ontology may be represented as a directed graph comprising nodes, the nodes representing defined concepts and connected by arcs—relationships. Such definitions are described as description logics. In Noy N F, McGuinness D L. Ontology development 101: A guide to creating your first ontology, an ontology is notably defined as a formal explicit description of concepts in a knowledge domain (classes or concepts), the properties of each concept describing the features and various attributes of the concept (also termed roles or properties), and restrictions on the attributes (also termed role restrictions). A 'reasoner' (computer tool) based on the various formal definitions of entities and concepts of an ontology may be used for inferring new knowledge in the form of facts. In addition, a 'fact' conceptually designates the representation of an action or a notion in the form of triplets. For example:

DOLIPRANE_BIOGARAN_1G PELL→"is a"→PHARMACEUTICAL_SPECIALITY

By linking these various entities (concepts and relationships), inferences may be obtained according to the nature of the relationships. Thus, if the relationship '→' is transitive: for A→B→C, it is inferred that A→C Multiple natures may be described in the representation format of description logics. A 'reasoner' then represents the engine based on these different natures of the linked entities in order to infer new knowledge.

As used here, a 'pivot ontology' designates an ontology containing at least two connections, to at least two other independent ontologies. It thus forms a composition reflective of multiple other ontologies of the same knowledge domain in order to facilitate and better represent a notion, a concept through multiple formal definitions. A preliminary method may be applied in order to choose and (re)form the sought definitions. This pivot aspect makes it possible to quickly interlink data separately annotated by these different ontologies which were not originally intended to be interoperable.

As used here, an "annotation" refers to a label assigned above an object. An annotation thus makes it possible to provide a reference point above an object which is lacking any.

As used here, a "knowledge base" (also referred to here as a 'database') designates an ontology and a set of individual class instances (Noy N F, McGuinness D L. Ontology development 101: A guide to creating your first ontology). A drug knowledge base, according to the invention is thus a pivot ontology instantiated with data describing the drug domain. A knowledge base is thus associated with an instantiation of the pivot ontology with actual data originating from free access open data (e.g. public drug databases, Health Insurance, etc.).

A 'structuring' designates a reentrant process via the use of a knowledge base and the reasoner in order to give meaning to a datum. Based on the different formally described notions, structuring not only allows a labeling via textual similarity measures, but also a semantic labeling. The annotation method may use a step of structuring in order to provide a disambiguation by then providing a semantic context (semantic annotation). For example, the datum given below may be considered as elementary knowledge which may then be integrated into the knowledge base (reentrant aspect):

"I have a heart problem"→heart the myocardium?, cardiac problem?

As used here, an "extraction" designates a functionality for making annotation/structuring possible above more or less structured data. For example, for tabular data, this makes it possible to take into account the different columns and perform alignments between similar notions by means of annotations and to provide a context (usage, definition) by means of a structuring. Since each source datum possesses a heterogeneous nature, specific tools may be used for its deserialization and its comprehension. Extraction makes it possible to establish a link between the structured vocabularies and the actual data.

The pivot drug database 10 thus generated according to the embodiments of the invention may be used in a drug-related analysis tool or device 20 such as a drug interaction analysis device or a tool for assisting medical prescription. The analysis device 20 may interact with client devices 50 according to a client/Server architecture: the client devices 50 may transmit queries according to a query language (e.g. SPARQL) and/or a protocol chosen via a graphical user interface 60. In response to these queries, the server 200 of the analysis device 20 may query the common database 10 and generate a display of the results which are returned to it via the graphical interface 60. In applications of the invention of the drug interaction analysis device type (pharmacology), the display of the results may be generated in the form of diagrams and/or data, for example. In applications of the invention of the tool for assisting medical prescription type, the display of the results may be generated in the form of an editable file in the medical prescription format, the client device user (family practitioner or specialist) being able to edit or complete the prescription before finalizing it. The common database 10 may be associated with a database management system for monitoring the database and access to its contents, as well as application functions and/or a set of rules defining the rules of access to the data. Each client device 50 may be an electronic device that includes the hardware, software, or integrated logic components capable of executing functionalities. Examples of client devices 50 may include a computer system such as a desktop computer, a mobile electronic device such as a laptop, tablet, cell phone, smartphone, etc. Each client device 50 may allow its user to communicate with the analysis device via a network 3 by using a graphical user interface 60 and a command input (manual or voice), etc. The user interface may form part of a dedicated WEB application, and be in the form of dedicated WEB pages.

More generally, the client devices may use any Human-Machine Interface functionally coupled with one or more processors of the computer system on which the analysis device 20 is implemented and allowing a user to interact directly with this computer system. The Human-Machine Interface (HMI) may include a video or alphanumeric display, a touch screen, a speaker and any other visual and audio indicator capable of communicating data to the user. The Human-Machine Interface (HMI) may also include input devices and controls such as an alphanumeric keyboard, a pointing device, keypads, push-buttons, control buttons, microphones, etc., capable of accepting commands or inputs from the user and transmitting them to the processor(s) of the computer system.

The device 100 for generating a pivot database 10 may be connected at the input to one or more data sources 2. The data sources 2 may be heterogeneous databases storing data, each datum being associated with a drug according to any format or specific storage structure such as, for example:

- databases of the "Product Characteristics Recommendations" (PCR) type, or
- databases, of the "Marketing Authorization" (MA) type.

The data sources 2 may comprise data sources provided for taking into account the different actors of the drug, such as, for example:

- pharmaceutical laboratories, researchers, innovators and drug producers; commercial companies distributing drugs;
- regulatory bodies such as the National Agency for Drug Safety and Health Products (ANSM) and the National Health Authority (HAS) which authorizes the marketing of drugs, and/or sets drug prices;
- healthcare professionals and healthcare prescribing establishments;
- drug consumers (patients);
- drug purchasing premises,
- dispensaries and healthcare institutions;
- health cover bodies, namely sickness insurance companies and complementary bodies.

The data sources 2 may, for example, comprise:

- databases generated by private bodies (Thériaque, Vidal, Claude Bernard, mutual funds, insurances);
- public databases: sickness insurance, ANSM in conjunction with the HAS;
- unstructured data sources generated by healthcare bodies and professionals comprising product characteristic summaries and adverse effect reporting forms;
- unstructured data sources generated by patients such as social networks or forums, for example.

The data sources 2 may be constructed using different classifications in the drug domain.

For example, some data sources 2 may use the ATC (abbreviation for "Anatomical Therapeutic Chemical classification system") classification. This ATC classification, published by the World Health Organization (WHO) comprises a classification of the "active ingredients" or "active substances" according to the organ or system on which they act, and their therapeutic and pharmacological properties.

The ATC classification comprises 5 levels of hierarchy:
- a 1st level corresponding to the main anatomical class;
- a 2nd level corresponding to the therapeutic subclass;
- a 3rd level corresponding to the pharmacological subclass;

a 4th level corresponding to the chemical subclass; and a 5th level corresponding to the active substance.

An example of ATC classification of Clindamycin is given below:

J ANTIINFECTIVES FOR SYSTEMIC USE

J01 ANTIBACTERIALS FOR SYSTEMIC USE

J01F MACROLIDES, LINCOSAMIDES AND STREPTOGRAMINS

J01FF Lincosamides

ATC Code Name

J01FF01 clindamycin

In an ATC type classification, an active substance may be classified multiple times, according to very different codes, and at all levels. For example ASPIRIN "UPSA 325 mg" has the code ATC B01AC06, which corresponds to the pharmacological subclass of antithrombotics, while ASPIRINS "UPSA 500 mg" and "UPSA 1000 mg" both have the code ATC N02BA01, corresponding to analgesics and antipyretics.

It should be noted that the indications of the active ingredients vary from country to country, according to the Marketing Authorizations (MA) obtained, the same active principle will therefore have different ATC codes in different countries.

It should also be noted that the notion of active substance is not specifically defined, and that the ATC classification is generally considered as classifying "drugs". For a given drug, it may (rarely) happen that another code is used when the official ATC classification refers to an organ and to therapeutic characteristics that do not correspond to the MA issued in France. Furthermore, some combinations of active ingredients (e.g. clavulanic acid+amoxicillin) have their own 5th level ATC code.

Other data sources 2 may use the INN (International Nonproprietary Name) classification.

International Nonproprietary Names (INNs) identify "the pharmaceutical substances or active pharmaceutical ingredients" (WHO). Each INN is a unique appellation that is globally recognized and which belongs to the public domain. It is also known as a generic name.

The names of the salts and esters having the same active substance exhibit a difference with respect to the inactive fragment of the molecule (oxacillin and ibufenac are INNs and their salts respectively bear the names sodium oxacillin and sodium ibufenac). The latter names are modified INNs (INNMs).

The designation of "modified INN" may also be used for a base or an acid. For example, the name "sodium levothyroxine" was published as an INN; that of "levothyroxine" may therefore be described as an INNM.

Other data sources 2 may further use the CIS (Code Identifiant de Spécialité—Proprietary Medicinal Product Identifier Code) classification which designates the proprietary medicinal product corresponding to the drug in its marketed form, therefore comprising a brand name, and completed with a dosage and a galenic form. The CIS code is a numerical 8-digit code which makes it possible to identify a drug regardless of its presentation (or packaging). It is allocated by the ANSM.

Some data sources may further be constructed according the CIP (Code Identifiant de Présentation—Presentation Identifier Code) classification which designates the presentation corresponding to the drug in its packaged form. Each presentation of a proprietary medicinal product is identified by a "CIP code". A presentation (and only one) is defined by the following elements:

its name (brand name)

its pharmaceutical (galenic) form its dosage its packaging and the capacity of its packaging.

The CIP classification is associated with a 13-digit code (e.g. 3400930000120) comprising:

The prefix of the drug France, an additional position for drugs with MA, a 7-digit code, a check key.

The 13-digit CIP code is encapsulated in a coding data array comprising a batch number and the expiration date in addition to the 13 digits. The 13-digit code is mentioned in the marketing authorization decision (decision and its annexes) of any proprietary medicinal product. For the same CIS code, there are several CIP codes, according to the presentation.

Another classification that may be used by a data source 2 may be the UCD (Unites Communes de Dispensation—Common Dispensing Units) classification. UCDs are issued in healthcare establishments. There is a correspondence between the UCD code and the ATC code.

Some data sources may further use the EPHMRA Anatomical Classification. This classification is maintained by the European Pharmaceutical Marketing Research Association (EphMRA). It describes therapeutic classes in which molecules, combinations of molecules or proprietary products are all equally classified. Unlike the ATC, and despite its similarities, the EPHMRA code has no particular meaning in its breakdown, with the exception of the first letter, and the number 9 meaning "others". The code sequence does not imply any priority or particular meaning.

It should be noted that the same class or subclass defined in several drug classifications may be different from one classification to another or more generally from one data source 2 to another when these data sources are based on different classifications. For example, the same class or subclass may differ in its label which may be slightly modified according to the data sources (and therefore the classification that they use), or in their semantics which do not describe the same cross-references.

For example, the therapeutic classes vary from one data source to another. Thus, in the case of drug interactions, the therapeutic classes defined by the ANSM are different from those of the ATC. The EPHRMA classes are also different.

The person skilled in the art will appreciate that the classifications used by the different data sources are not limited to the examples cited above and may include any classification or representation relating to drugs.

The data sources 2 may therefore be based on a great variety of classifications in the drug domain and constitute a set of very heterogeneous data sources forming a set of fragmentary information, of different granularities, and described with different classifications.

The device 100 is suitable for homogeneously integrating this plurality of data sources.

Figure 2:
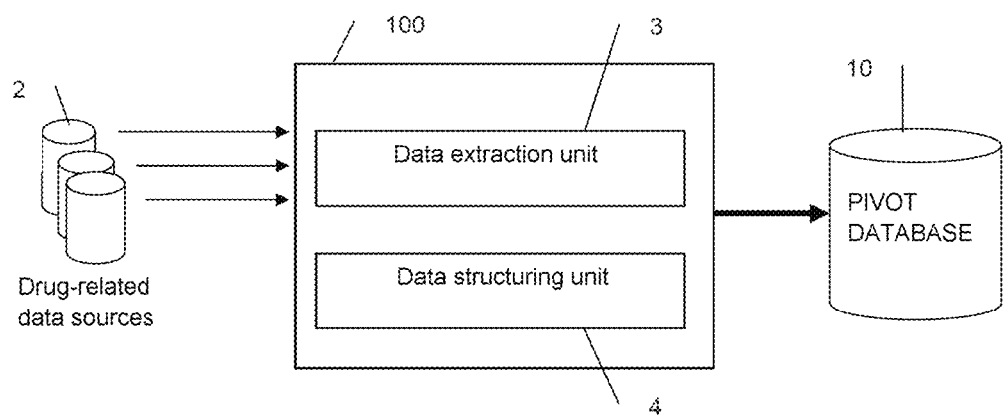
FIG. 2 is a diagram representing the device for generating the pivot drug database, according to one embodiment.

With reference to FIG. 2, the device 100 for generating the pivot database may comprise:

a data extraction unit 3 for extracting the heterogeneous data derived from the different data sources 2; the extracted data may be referred to hereinafter as "initial data" or "unstructured data" for designating this data organized according to the heterogeneous formats/representations of the different data sources 2, some sources comprising drug-related data which may not fit the standard medical semantics (e.g. Internet forum data sources);

a data structuring unit 4 configured for structuring the extracted data by applying a pivot drug ontology 40 to the extracted data; the data obtained after processing by the structuring unit 4 will be referred to hereinafter as "structured data".

The data thus structured is then maintained/stored in a pivot database 10 comprising entries, each entry storing attributes associated with a value corresponding to the classes of the pivot ontology.

The data stored in the data sources 2 and in the pivot database may be represented by a graph. In some embodiments, the data sources 2 and those of the pivot database 10 may be specialized databases based on such graphs for ensuring the persistence of the data and may be associated with semantic resources based on facts of the type: subject/predicate/object ("triplestores").

Figure 3:
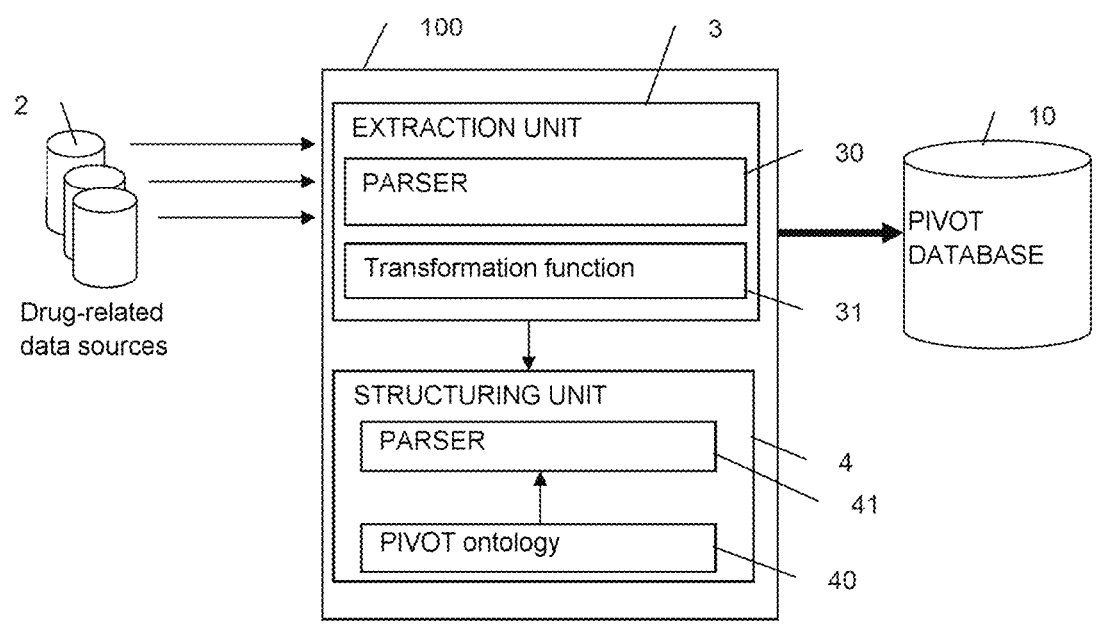
FIG. 3 is a diagram representing the device for generating the pivot drug database, according to a variant embodiment.

Reference is made to FIG. 3 which represents the device 100 for generating a database according to some embodiments.

In such embodiments, the data extraction unit 3 may comprise a first parser 30 for scanning the drug data of the different sources 2. In one embodiment, the data may be retrieved from the different sources 2 in the form of one or more data description files in a first format (also termed an "initial format", e.g. in the PDF format (Portable Document Format)). The first parser 30 may be configured for scanning the data or description files in the initial format and transmitting the scanned data to a transformation function 31 configured for transforming each data description file derived from the source databases 2 into a data description file in a second editable format (e.g. a file in the text format (txt)).

In some embodiments, the structuring unit 4 may be configured to search for similarity information between the data extracted from the data sources 2 by scanning each description file converted into the second format (also termed the "target format"). A second parser 41 may be used to search for the similarity information with the concepts or classes of the pivot ontology 40. In response to the detection of similarity information data in relation to the concepts or classes of the ontology, the similarity information may be collected then analyzed for associating the scanned data with classes and relationships of the ontology (instantiation of the concept or of the class of the ontology). This instantiation results in the construction of a graph representing the relationships between the detected classes corresponding to the scanned data.

The data thus structured are stored in the pivot database 10 from the graph obtained.

The structuring unit 4 is thus configured for "contextualizing" the heterogeneous data extracted by the extraction unit 3, which allows it to be best exploited.

As used here, the operation of "contextualization" performed by the structuring unit 4 consists in applying the ontological model 40 of the drug (known as the "pivot ontology") to the data extracted by the extraction unit 3. The pivot ontology makes it possible to formally represent the useful and usable data in the drug domain for allowing their use in applications relating to the analysis of drug interactions or for assisting prescription (generation of drug-related recommendations).

Such an operation of "contextualization" of the data helps transform the heterogeneous data sources 2 (also termed "elementary data sources") into a pivot knowledge base 10 in which the extracted heterogeneous drug-related data is maintained according to a common structure.

Such a pivot knowledge base 10 is suitable for executing complex queries appropriate to exploiting the diversity and exhaustiveness of the data stored for applications relating to analyzing interactions between drugs, by taking into account the characteristics specific to the drugs (e.g. the therapeutic class, the dose, etc.). The enriched knowledge base 10 as generated by the device 100 therefore allows numerous drug-related analysis applications (e.g. study of new relationships not present in the original data).

The termino-ontological sources and resources in the drug domain, and more generally in the biomedical domain may be very numerous. As a result, some of the concepts used in relation to drugs in these sources and/or resources may be represented or described heterogeneously, their representation or their definition not being shared by all the sources/Resources.

For grouping the extracted data in the structured database derived from these various sources, the structuring unit 4 of the device 100 for generating a pivot drug database may be configured for homogeneously structuring the extracted data by applying a new pivot ontology. The structuring unit 4 may be configured for instantiating such a pivot ontology 40 of the drug with the extracted data, the ontology meeting a technical constraint appropriate to the drug domain.

The structuring unit 4 thus offers a modular approach to drugs, which ensures more flexibility in the tools that rely on the heterogeneous knowledge base obtained while making it possible, for specific cases of use, to reuse specific ontologies or models, such as the DIDEO model for drug interactions, for example.

More precisely, the structuring unit 4 may implement a pivot ontology 40 based on a systematic and logical breakdown of a generic drug concept termed "Drug" according to the elementary concepts that compose it.

The RxNorm model developed and maintained by the US National Library of Medicine, within the Unified Medical Language System (UMLS), provides standardized drug names related to the main existing databases (such as "First Databank", "Micromedex", "MediSpan", "Gold Standard Drug Database", etc.). RxNorm incorporates the NDFRT ontology. RxNorm conventionally serves as a tool and support for interoperability between drug terminologies and knowledge bases. RxNorm, in its publicly available versions, has 118555 concepts, corresponding to drugs. The RxNorm model is constructed from three founding entities: ingredient, galenic form and dose, which when combined, form the concept of "Clinical Drug".

For example, in comparison with the conventional semantic model RXNORM, the structuring unit 4 applies a new ontology to which is added this concept "Drug", which allows links notably to CHEBI (ChEBI designates the ontology "Chemical Entities of Biological Interest Ontology" which structurally classifies chemical and biochemical components; ChEBI is a chemical ontology, allowing relationships between molecular entities or classes of entities to be described in a structured way). In addition, the applied ontology comprises a restricted number of relationships between concepts, which makes it possible to limit the conflicts that exist in the conventional models (e.g. RXNORM).

Furthermore, while the provided ontology may be represented in OWL, there is no available representation of the RXNORM semantic model in OWL.

By structuring the data with the pivot ontology applied by the structuring unit 4, the provided device supplies a heterogeneous knowledge base which may be queried with any query language or protocol that makes it possible to search, add, modify or delete RDF (Resource Description Framework) data available through the Internet such as SPARQL (Protocol and RDF Query Language).

The semantic models conventionally used for representing drug data such as RXNORM do not allow querying the knowledge base storing this structured data by means of such query languages.

In some embodiments, the structuring unit 4 may be configured for instantiating the drug data extracted in the pivot ontology 40 of the drug, by using an application programming interface (API) of the knowledge representation language OWL for selecting for each element of the database the corresponding concept in the semantic model of the pivot ontology 40.

The data is held in a pivot knowledge base 10 thus structured.

The pivot knowledge base 10 thus obtained may receive queries in a suitable query language such as SPARQL queries. The queries that can be processed by the knowledge base may be preprogrammed. In response to a query, the heterogeneous pivot knowledge base 10 may export the result which may be displayed in a graphical interface configured according to the application of the invention.

Figure 4:
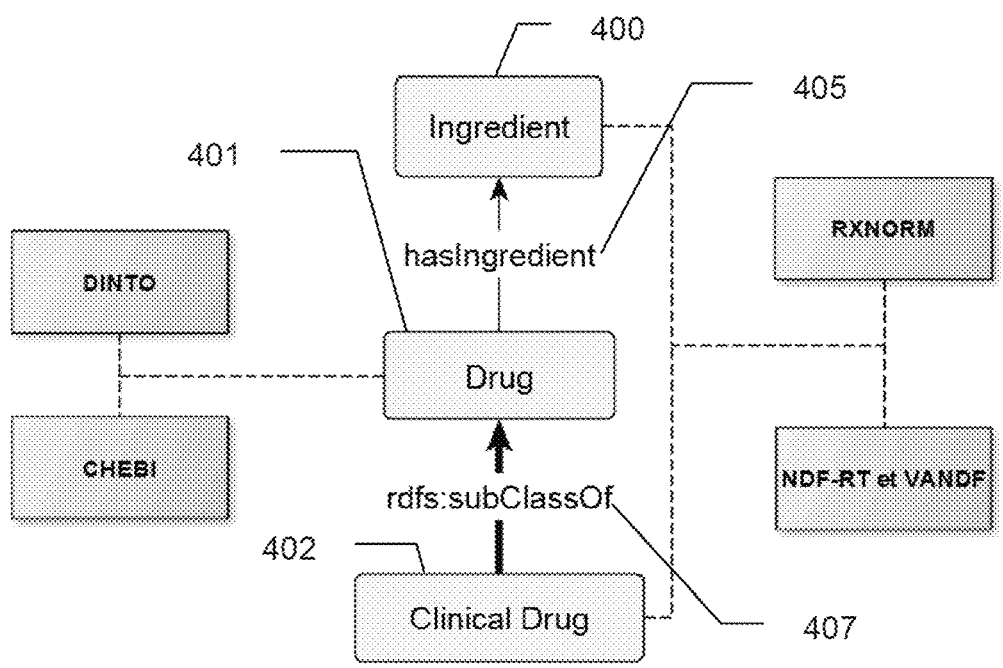
FIG. 4 depicts a simplified architecture of the ontology used by the structuring unit, according to some embodiments.

FIG. 4 depicts a simplified architecture of the pivot ontology 40 used by the structuring unit 4, according to some embodiments.

An ontology is conventionally defined as an explicit formal specification of a conceptualization, a "conceptualization" referring to a modeling of a phenomenon in the world by identifying the relevant concepts of this phenomenon. An ontology is "explicit" in that the type of concepts and constraints applied to the concepts are explicitly defined. An ontology is "formal" in that essentially an ontology is a specification that can be understood by a machine, unlike natural language.

More specifically, an ontology refers to a modeling of a set of data (or knowledge) in a given domain given in the form of:
 "Concepts" (also termed "classes"), a concept being the representation of an entity of the domain;
 "Properties" (also termed "attributes") related to the concepts.
 "Relationships" are used to represent the connection between concepts.

The ontological pivot model 40 may be used by the structuring unit 4 for integrating and/or processing data extracted from the heterogeneous data sources 2, but also for determining new relationships from fragmentary information derived from the extracted data or determining possible alignments between the data sources 2 (e.g. alignments between therapeutic classes as described in different sources 2).

It should be noted that the drug domain has a transverse positioning in connection with a plurality of related domains: it is related to the domain of pathologies and diagnosis, but also to biological mechanisms and genomic data, these domains being associated with specific ontological resources. The pivot ontology 40 may further be used by the structuring unit 4 for integrating such ontologies specific to these related domains from termino-ontological resources of the drug domain.

The ontological pivot model 40 may be based on one or more reference models, such as the RXNORM model.

The RxNorm model is the international reference. It breaks down the drug into its three fundamental concepts (galenic form, dose and ingredient). However, the concept Drug, as described, for example, in ChEBI, is not found in the RxNORM model. In addition, RxNorm does not have a "high level" model inferring the described relationships. Another drawback of RxNorm is the multiplicity of relationships present in this model (28 paths for the 8 main concepts): while these relationships allow passing through multiple "paths" to find information, they do not all give the same result.

The ontological pivot model 40 is constructed using a semantic representation language such as OWL which is based on a description logic. Other ontology representation languages may be used as an alternative such as OIL, DAML and DAML+OIL.

OWL has components consisting of classes, instances and properties of which there are two categories:
 object properties ("owl:ObjectProperty") which connect one object to another object, and
 type properties ("owl:DataTypeProperty") which connect an object to a type value.

There are 3 OWL sublanguages:
 "OWL Lite" which comprises simple constraints;
 "OWL DL" is a more expressive but decidable language;
 "OWL Full" which allows maximum expressivity but the decidability of which is not guaranteed.

As depicted in FIG. 4, the pivot ontology used 40 is based on a modular approach which makes it possible to establish correspondences ("mappings") with the existing drug ontologies (RxNorm, ChEBI, etc.). The pivot ontology 40 is based on key concepts comprising the concept Ingredient (400), the concept Drug (401), and the concept Clinical drug (402) as defined in ontological models of the drug. The concept "Drug" (401) is defined by ChEBI, the concept "Ingredient" (400) is defined by RXNORM. The concept "Clinical Drug" (402) is derived from RXNORM, the NDFRT and VANDF models, and is linked to the concept of "Drug" by the relationship defined in pseudo code "Clinical Drug rdfs: SubclassOf Drug" (the concept "Clinical Drug" is a subclass of the concept "Drug").

These three key concepts are defined as follows:
 The concept of interest "Ingredient" (400) designating "a compound or therapeutic moiety giving the drug its clinical properties" (as defined in the RxNorm terminological resource);
 The concept of interest "Drug" (401) designating: "Any substance which, when it is absorbed by a living organism, may modify one or more of its functions. The term is generally accepted as a substance taken for a therapeutic purpose, but is also commonly used for drugs ('abused substance)" (as defined in the ChEBI ontology);
 The concept of interest "Clinical Drug" (402) designating an "entity composed of the concepts Ingredient, Dose and DoseForm (galenic form)" (as defined in the RxNorm terminological resource).

The concept of interest "ingredient" (400) may, for example, correspond to the INN classification and the concept "clinical drug" (402) may correspond to the CIS classification.

Each module 400, 401, 402 of the ontology is independent and may be developed separately.

Such a modular approach is particularly suited to a drug pivot ontology, the existing ontologies being very numerous, and the drug being, by definition, in relationships with a multitude of other related concepts or domains (symptoms, diseases, mechanisms of biological action, etc.) which are associated with numerous specific knowledge models.

In a preferred embodiment, the concept "Drug" (401) may be modeled in the form of a class according to the ontology representation language used (e.g. OWL class) and is used as the top class in accordance with the ChEBI ontology definition:

the concept "DRUG" 401 has one or more "Pharmaceutical Ingredients" for ingredient, the concept "DRUG" 401 has at least one "Pharmaceutical Ingredient", the concept "DRUG" 401 only has "Pharmaceutical Ingredients" for ingredient.

In the embodiment considered, the top concept "Drug" is the parent of 9 entities, these "child" entities being modeled in the form of classes in the ontology representation language used (OWL classes, for example) and comprising the classes:

For the "clinical" part of the model: "Clinical Drug", "Clinical Drug Component", "Composed Clinical Drug Component", "Clinical Drug Form", "Composed Clinical Drug Form", For the "commercial" part of the model: "Branded Drug", "Branded Drug Component", "Branded Drug Form" and "Brand Name".

Classes bearing the same label as the concepts of the RxNORM ontology may describe the same concepts. The concept "Clinical Drug" is therefore derived from the composition of 3 other entities according to this embodiment: Ingredient, Galenic form (DoseForm) and Dose (concepts derived from the RxNorm ontology).

The concept "Clinical Drug" may itself be defined as a child of the "ClinicalDrug Component" class and of the "Clinical Drug Form" class, any instance of the "Clinical Drug" class also being an instance of these two classes.

The combinations of the concepts "Ingredient-Dose" and "Ingredient-DoseForm" respectively give the concepts "Clinical Drug Component" and "Clinical Dose Form". These two concepts, as well as the concept "Clinical Drug" may be broken down into a commercial part (Branded part) of the model which corresponds to drugs bearing a trademark. The concept "BrandName" corresponds to the brand name of the drug, such as "Doliprane".

Figure 10:
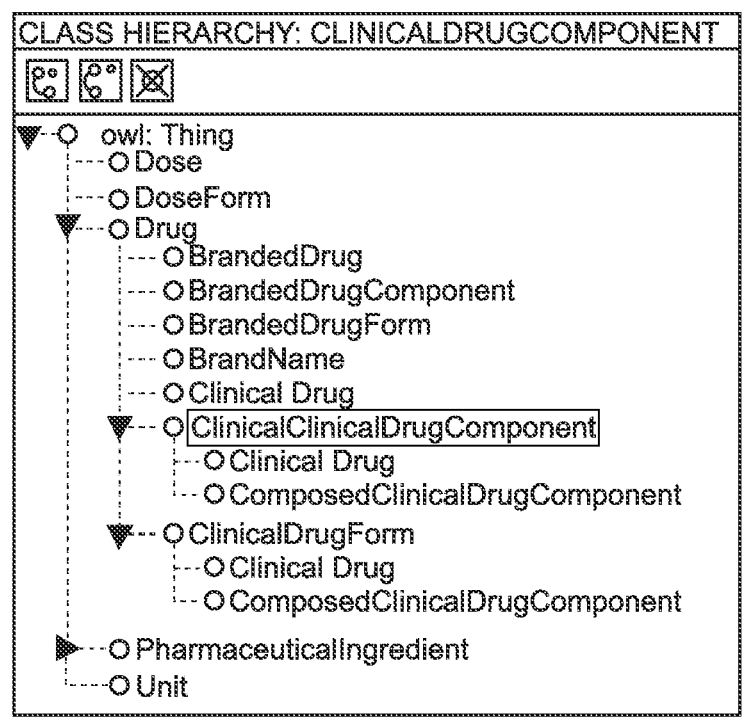
FIG. 10 lists a first example in pseudo-code mentioned in the description.

FIG. 10 depicts the hierarchy of the pivot ontology 40, in OWL, according to one embodiment.

The concepts of the pivot ontology 40 are all subclasses of the concept "Drug" (related to the concept Drug by the relationship "rdfs:SubClassOf Drug"). The concept of "Drug" is connected by the relationship "has_ingredient" to the concept of "Ingredient". Some restrictions may also be implemented.

Figure 11:
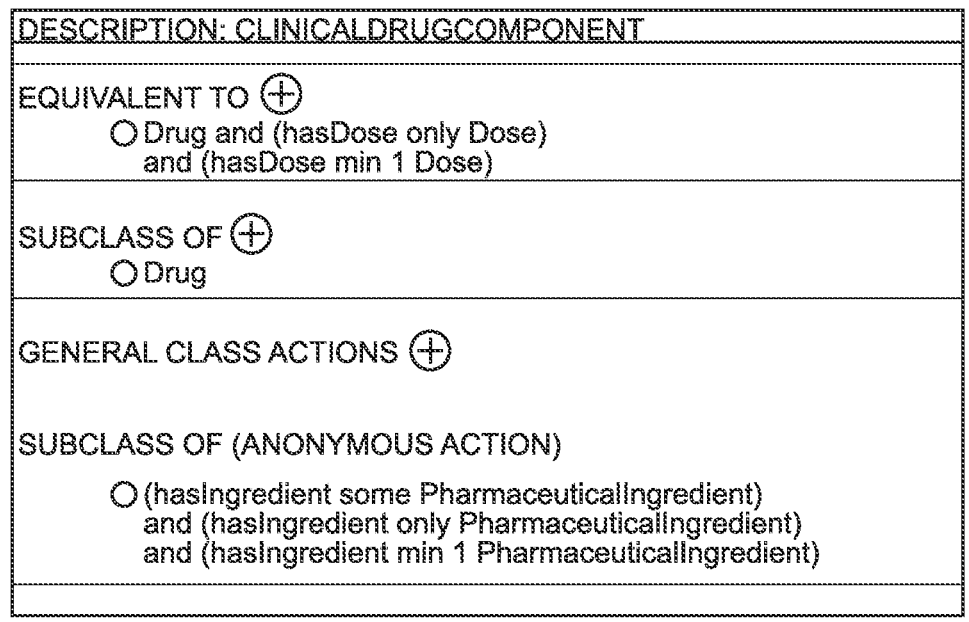
FIG. 11 lists a second example in pseudo-code mentioned in the descriptions.

For example, the concept of "ClinicalDrugComponent" may be described in OWL as in FIG. 11.

In description language, the pivot ontology 40 may be described as in FIG. 12.

The pivot ontology 40 has been compared with classes described by the ATC at the 2nd ("2 digit") level and the classes described by the Thesaurus of interactions of the ANSM. The classes corresponding to the last ATC level (7 digits), and to the second (2 digit) level as well as an ANSM Family class have been created with the aid of the OWL API Application Interface from the data describing the ANSM classes, constructed from the thesaurus of drug interactions. The "OWL API" Application Interface is a JAVA API for creating, manipulating and serializing termino-ontological resources in OWL format.

A relationship "appartientA" ("belongsTO") has been created. The hasIngredient relationship was present between BrandedDrug and PharmaceuticalIngredient, inferred through Drug.

A query in SparQL was then made in order to find all the ANSM and ATC2 classes for which the label of the instances of FamilleATC5 (ATC5 Family) were identical to the label of PharmaceuticalIngredient. The SparQL query was used for displaying the results as illustrated in FIG. 5.

In considering the example of the acebutolol molecule, it may be noted, according to the table in FIG. 5, that this molecule belongs only to the therapeutic subclass of beta blockers in the ATC. On the other hand, in the thesaurus of drug interactions of the ANSM, this molecule is classified into five different classes: i) antihypertensives except alpha blockers, ii) beta blockers (except esmolol and sotalol) iii) beta blockers (except esmolol) iiii) bradycardiac, in) blood pressure lowering drug.

Figure 6:
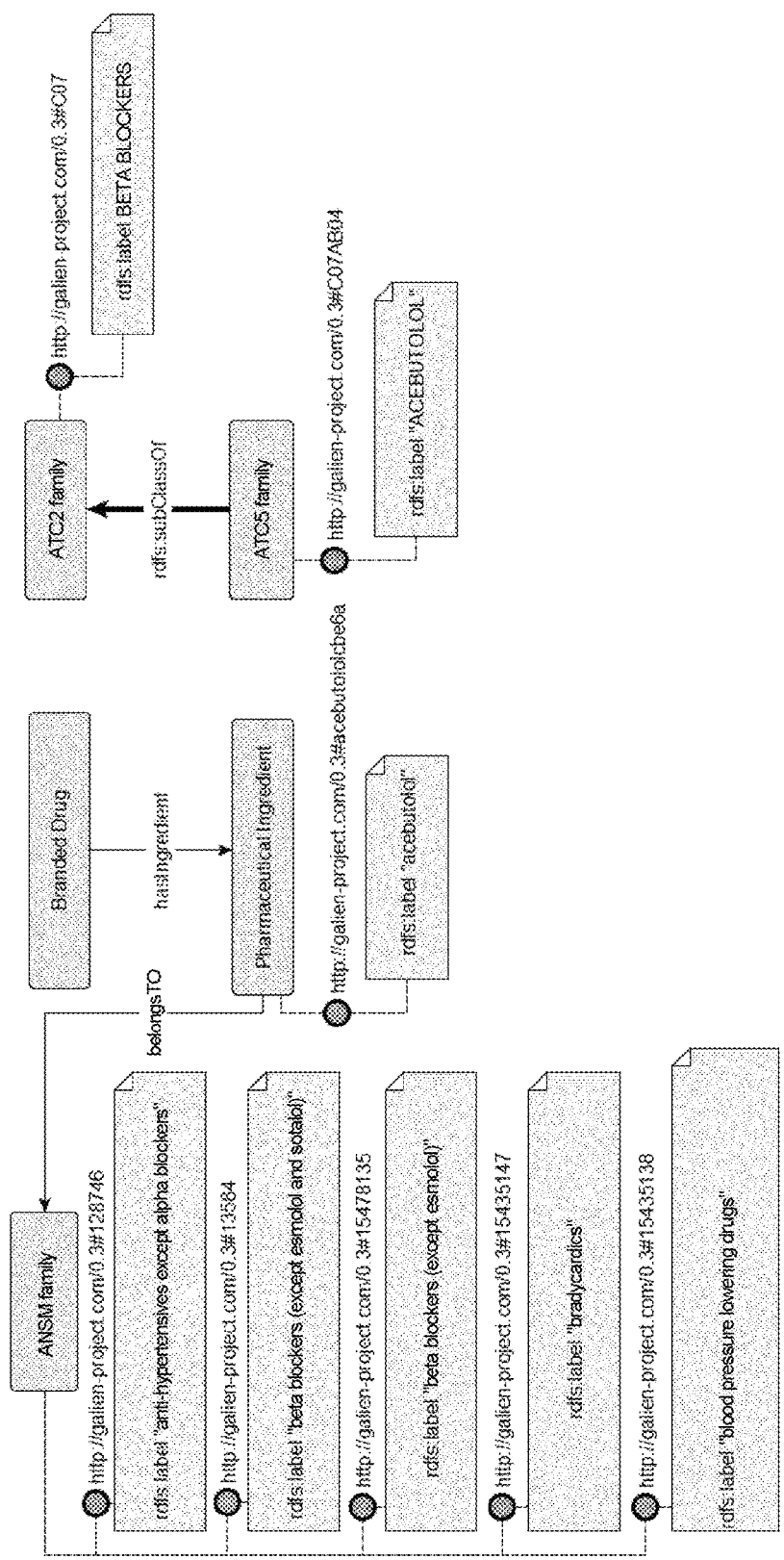
FIG. 6 represents the results of the comparison of classes for ACEBUTOLOL.

A complete lack of agreement between the ATC and ANSM labels may be observed. However, the pivot ontology 40 used makes it possible, by means of the concept "pharmaceuticalIngredient" and by using the "ANSM" and "ATC" modules independently, according to the modular approach implemented by the device 100, to find that beta blockers are potentially a class serving to "lower blood pressure", "bradycardiac" as illustrated in FIG. 6, which represents the result of the comparison of classes for acebutolol.

Figure 7:
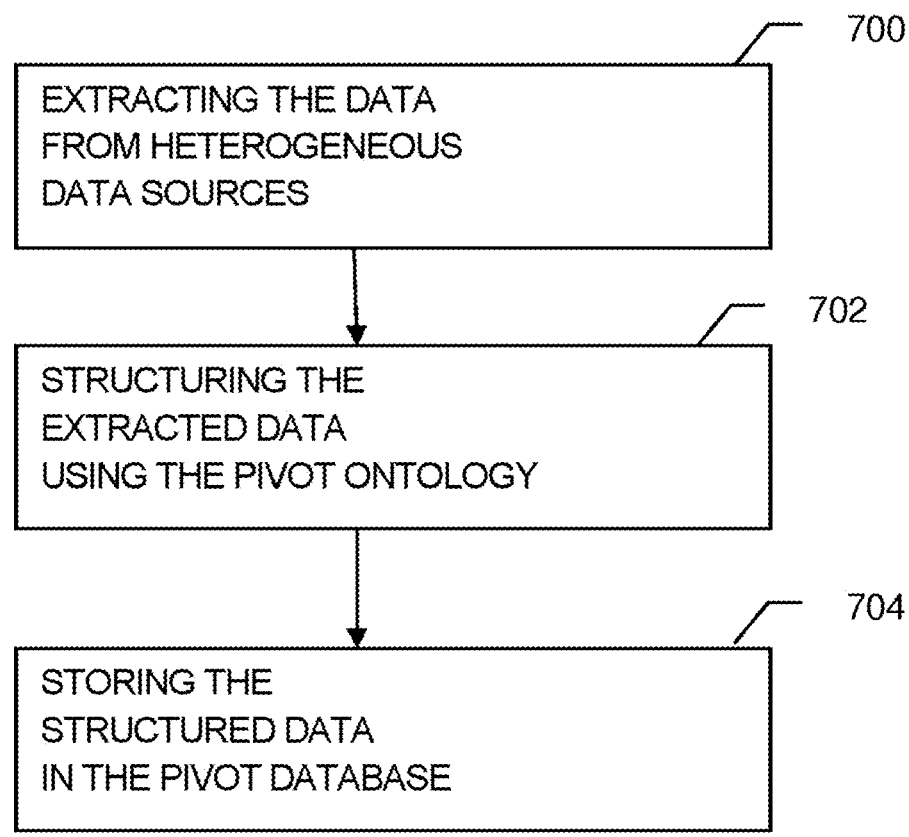
FIG. 7 is a flow diagram illustrating the method for generating the pivot drug database according to some embodiments.

FIG. 7 represents the method for generating a knowledge base according to some embodiments.

In step 700, the unstructured data relating to drugs is extracted from the data sources 2.

In step 702, the pivot ontology, previously loaded, is applied to the extracted data (step of instantiation of the ontology) and the pivot database 10 is generated in step 704. Step 702 may comprise the scanning of the extracted data using a parser 30 to apply the pivotal ontology to the extracted data.

The information thus extracted (structured data associated where applicable with a category) is thus grouped in a structured database 10 coming to enrich the already existing heterogeneous databases 2 while offering centralized access to the heterogeneous drug data in a structured format.

Figure 8:
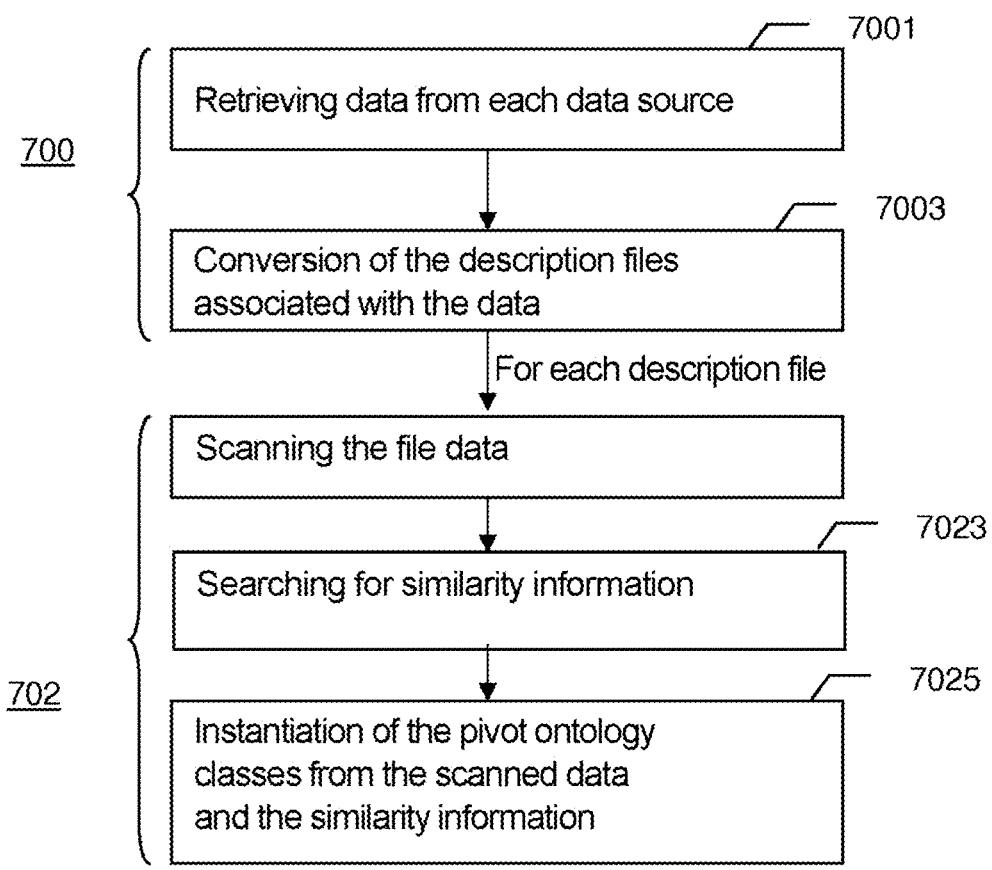
FIG. 8 is a flow diagram illustrating the method for generating the pivot drug database according to one embodiment.

FIG. 8 represents the method for generating the pivot drug database according to one embodiment.

In one embodiment where the heterogeneous data is retrieved from the data sources in the form of a description file having a first format, the step of extraction 700 may comprise:

a step 7001 of retrieving data from each data source 2 in the form of at least one description file in a first format (e.g. a "PDF" format);

a step 7003 of conversion or transformation of the description files associated with the data retrieved from each data source 2 into a second format (e.g. "txt"), by scanning each description file (7002) by means of a parser 30 and by converting the scanned information according to transformation rules ("mapping rules"), the transformation rules defining the correspondences for passing from the first format to the second format.

The format of the description file (first format) may be different for the different data sources 2. The format (second format) into which each description file extracted from the data sources 2 is converted may advantageously be the same whatever the original formats of the extracted description files (first formats).

The step of instantiation of the ontology 702 may then comprise the scanning of each description file in the second format 7021, and the instantiation of the classes of the ontology from the scanned data 7025 for each scanned file. For example, if the description files of the extracted data are files in a CVS format (second format), step 7021 may comprise the scanning of each CSV file then the instantiation of a class of the pivot ontology from the identified information 7025. Step 702 may comprise a search for semantic similarity information 7023 among the scanned data corresponding to the data extracted from the data sources 2 and the concepts of the pivot ontology. The detected similarity information may then be associated with concepts or classes of the pivot ontology (e.g. the "indications" class, the "contra-indications" class, the "known interactions" class, the "AM date" class, etc.). The data extracted from the initially unstructured data sources 2 is then structured by assigning it the concepts or class of the pivot ontology.

In some embodiments, the pivot database 10 may be used in a drug-related analysis device or tool 20 comprising a graphical user interface configured according to the application of the invention (prescription assistance, pharmacovigilance, etc.). The device 20 may be implemented in the form of a tool shared by multiple client devices via a network (the analysis device 20 being capable of being implemented in the form of a WEB application tool) or a device 20 configured for the use of each client device. Queries may be entered in the graphical user interface 60, for example, by entering the drug names in fields provided on the graphical user interface. Validation of the query (e.g. SPARQL) by the user causes querying of the database. In response to this query the knowledge base returns the result of the query, the tool 20 generating the display of the results on the graphical user interface based on the representation of the data of the pivot ontology. The display of the results depends on the application of the invention and the configuration of the graphical user interface 60. For example, a SPARQL query may be issued by entering a drug or a molecule for querying the data of the heterogeneous knowledge base which is contained in the concept equivalent to the molecules or drugs. In another example, multiple drugs may be entered on the graphical user interface, the execution of the SPARQL query triggering the search in the heterogeneous knowledge base for drug interactions between the drugs entered.

In one application of the invention, the pivot database 10 may be used in a device 20 configured for managing drug interactions. A drug interaction (Drug-Drug Interaction: DDI) refers to the effect that results from the concomitant or successive administration of two or more drugs.

An interaction has a "significant, described or potentially serious clinical expression", i.e. capable of "causing or increasing side effects" or "of leading, by reduced activity, to less treatment efficacy." (Source ANSM). Known DDIs are described in references, such as the Thesaurus of drug interactions, published by the ANSM every 6 months, and which describes the interactions as follows:

"The interaction is defined by a pair of protagonists "a+b" which may be: an active substance, designated by its international nonproprietary name (INN) or a therapeutic class, itself forming the subject of "class" interactions."

The pivot database 10 allows efficient management of the DDI and limits the number of annual deaths related to DDIs (it is estimated that DDIs in France are responsible for 8 000 deaths a year in France and 130 000 hospitalizations). The DDI references may be used directly for prescription assistance and/or prescription analysis.

For example, the drug interaction analysis device 20 may be used for detecting whether a patient treated with "zyloric" can receive a penicillin. The pivot database 10 makes it possible, for example, to determine whether the active substance of "Zyloric" is allopurinol, to determine all the penicillin class drugs, among which the penicillin A subclass is found, for example, to search whether there are interactions between allopurinol and all the active substances included in the penicillins, and to deduce therefrom that the combination of "zyloric" and the drugs of the "penicillin A" subcategories is to be taken into account (amoxicillin, ampicillin, etc.) with regard to there being an increased risk of skin disease if these drugs are combined.

The device 20 for analyzing and managing DDIs makes it possible to remedy situations where the physician does not have all the information concerning the prescription in question or has incomplete or inaccurate information (i.e. "Augmentin" without dosage or dose form, or else "acetylsalicylic acid" (INN) without specifying the brand name).

In addition, it is possible to use additional data sources regarding DDIs and the potential interactions (PDDIs). Since DDIs are subject to change according to the dosage, galenic form, and even the indication for which the drug has been prescribed (source ANSM Thesaurus), it is particularly advantageous to process the information originating from a multiplicity of sources 2 on different semantic levels and at heterogeneous granularities (therapeutic classes and INN).

The analysis device 20 may also be used in applications for identifying the misuse of drugs in forums (pharmacovigilance). Indeed, some forums related to health may be an important source of data, supplied by patients about the actual use of the drug. This Internet Forum type data source 2 has an unstructured format for the data that it collects, as well as different types of granularity. Indeed, the users of these forums are often unlikely to supply all the information using suitable medical semantics (e.g. the notions of "dosage" or "galenic form"), and rather express themselves using the brand name of the drug (e.g. "Doliprane" or "Augmentin") or more general terms ("Antibiotic" or "Antidepressant"). The method and the device for generating a drug data pivot database 10 makes it possible to manage the information collected in such Internet forums in a centralized way, regardless of their level of granularity and the semantics used, by using the pivot ontology which matches a level of granularity and/or common semantics with such unstructured information. Such data sources may thus be transparently exploited in tools for identifying the misuse of drugs.

The person skilled in the art will appreciate that the invention is not limited to a use of the pivot database 10 in 20 for assisting prescription or for analysis of drug interactions but may be more generally used in any drug-related analysis device such as, for example, a "precision medicine" device for managing adverse drug effects, involving the optimization of treatments for each individual, etc.

Such analysis devices 20 make it possible to address important public health issues based on the exploitation of multiple data sources having heterogeneous representations or classifications, which may depend on different languages when they originate from multiple countries.

The device 100 for generating a pivot drug database 10 and the analysis device 20 thus make it possible to manage, integrate and exploit such heterogeneous drug-related data sources.

The person skilled in the art will appreciate that the methods according to the embodiments may be implemented in various ways by hardware, software, or a combination of hardware and software, notably in the form of program code that can be distributed in the form of a program product, in various forms. In particular, the program code may be distributed with the aid of computer-readable media, which may include computer-readable storage media and communication media. The methods described in the present description may notably be implemented in the form of executable computer program instructions by one or more processors in a computing device. These computer program instructions may also be stored on a computer-readable medium.

Figure 9:
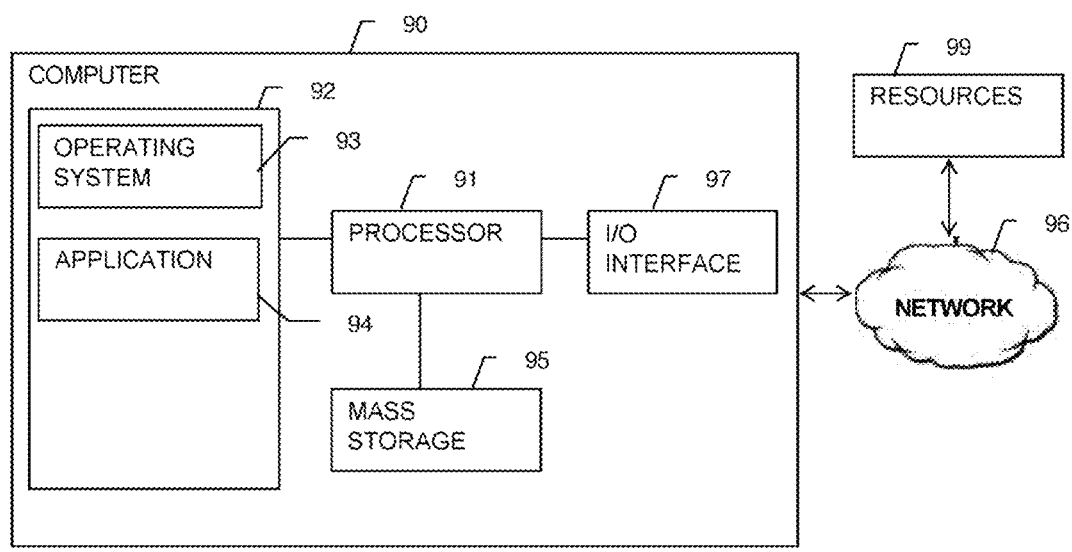
FIG. 9 is a schematic view of a computer system that may be used for implementing the device and the method for generating the pivot database according to some embodiments.

In particular, as illustrated in FIG. 9, the analysis device 20 may be implemented in the form of one or more computing devices or systems 90 (hereinafter referred to as a computer). The computer 90 may comprise a processor 91, a memory 92, a mass storage memory device 95, an input/output (I/O) interface 97 (e.g. video display, touch screen, input devices and controls such as an alphanumeric keyboard, a pointing device, numeric keypads, pushbuttons, control buttons, microphones, etc.). The computer 90 may also be functionally coupled to one or more external resources 99 via a network 96 and/or an I/O interface 97. The external resources 99 may include, but not be limited to, servers, databases, mass storage devices, peripheral devices, cloud-based network services, or any other appropriate computing resource that may be used by the computer 90.

The processor 91 may include one or more processor devices such as microprocessors, microcontrollers, central processing units, or any other device that manipulates signals (analog or digital) according to operating instructions that are stored in the memory 92. The processor 91 may operate under the control of an operating system 93 which resides in the memory 92. The operating system 96 may manage computing resources such as an integrated computer program code in the form of one or more software applications 94 residing in the memory 92.

The pivot database 10 may reside on a mass storage memory device 95. It may be used for collecting and organizing the data used by the various systems and modules of the computer 90. The pivot database 10 may include data and host the associated data structures which store and organize the data. In particular, the pivot database 10 may be organized in any form of database structure, notably, but not exhaustively, in the form of a relational database, a hierarchical type of database, a networked database, an object-oriented database, or combinations of these forms of databases. A database management system in the form of a computer software application that runs in the form of instructions on a processor (processor 91, for example) may be used for accessing the information or data stored in the pivot database 10 in response to a query, when the query is executed by the operating system 93, the applications 94, or one or more modules. The person skilled in the art will appreciate that the embodiments of the invention may use any appropriate database management model, and are not limited to a particular type of database.

The invention is not limited to the embodiments described above by way of non-restrictive examples. It encompasses all the variants of embodiment that a person skilled in the art might envision.

The invention claimed is:

1. A device for generating a pivot drug database implemented in a computer system, the device comprising:
    an extraction unit configured for extracting the data from a set of heterogeneous elementary drug data sources, the elementary drug data sources storing drug-related data, each elementary data source being associated with a representation of the data;
    a structuring unit configured for structuring the extracted data by applying a pivot ontology to said extracted data, said pivot ontology defining classes derived from one or more drug ontologies and relationships between said classes, which provides structured data associated with a graph representing the relationships between the classes corresponding to said structured data;
    the device being configured for generating said pivot drug database according to said graph and said structured data, the pivot database storing said structured data.

2. The device as claimed in claim 1, wherein the extraction unit is configured for retrieving the data of the elementary data sources in the form of a description file in an initial format, the extraction unit comprising a parser configured for scanning the data of each description file in the initial format and a transformation function for transforming the description file in the initial format into a description file in a target format, from the scanned data.

3. The device as claimed in claim 2, wherein the structuring unit comprises a parser configured for scanning each description file in the target format and for searching for similarity information between the scanned data and the classes of the pivot ontology, the structuring unit being configured for applying the pivot ontology to the scanned data by associating it with classes and relationships according to the similarity information, said graph representing the classes and said links.

4. The device according to claim 1, wherein the pivot ontology comprises three main classes:
    A main class "Ingredient";
    A main class "Drug"; and
    A main class "Clinical Drug",
    the three main classes being independent.

5. The device as claimed in claim 4, wherein the "Drug" class is the top class and comprises a set of subclasses.

6. The device as claimed in claim 5, wherein the subclasses comprise a set of "clinical" type classes and a set of "commercial" type classes.

7. The device as claimed in claim 4, wherein the top class "drug" is connected by a relationship of the "possesses" type to the "Ingredient" class.

8. The device as claimed in claim 1, wherein the pivot ontology is represented according to a chosen representation language.

9. A drug-related analysis device comprising:
    a server; and
    the pivot database generated by the device of claim 1, the device being capable of querying said pivot database in response to at least one query received from a client device and returning the result to the client device.

10. The drug-related analysis device as claimed in claim 9, wherein the analysis device is a device for assisting medical prescription.

11. The drug-related analysis device as claimed in claim 9, wherein the analysis device is a drug interaction analysis device.

12. A method for generating a pivot drug database implemented in a computer system, the method comprising the steps of:
    selecting a set of heterogeneous elementary drug data sources storing data relating to drugs, each elementary data source being associated with a representation of the data;
    extracting the data from said drug data sources;
    applying a pivot ontology to said extracted data, said pivot ontology defining classes derived from one or more drug ontologies and relationships between said classes, which provides structured data associated with a graph representing the relationships between the classes corresponding to said structured data;

generating a pivot database from said graph and from said structured data, the pivot database storing said structured data.

\* \* \* \* \*